United States Patent
Lavanya et al.

(10) Patent No.: US 12,258,523 B2
(45) Date of Patent: Mar. 25, 2025

(54) VALUABLE CHEMICALS PRODUCTION FROM CO-LIQUEFACTION OF BIOLIQUOR AND BIOMASS

(71) Applicant: HINDUSTAN PETROLEUM CORPORATION LIMITED, Maharashtra (IN)

(72) Inventors: Meesala Lavanya, Karnataka (IN); Pedapati Chakradhar, Karnataka (IN); Kumar Pramod, Karnataka (IN)

(73) Assignee: HINDUSTAN PETROLEUM CORPORATION LIMITED, Maharashtra (IN)

( * ) Notice: Subject to any disclaimer, the term of this patent is extended or adjusted under 35 U.S.C. 154(b) by 0 days.

(21) Appl. No.: 18/025,310

(22) PCT Filed: May 26, 2022

(86) PCT No.: PCT/IB2022/054956
§ 371 (c)(1),
(2) Date: Mar. 8, 2023

(87) PCT Pub. No.: WO2023/180798
PCT Pub. Date: Sep. 28, 2023

(65) Prior Publication Data
US 2025/0002789 A1    Jan. 2, 2025

(30) Foreign Application Priority Data
Mar. 25, 2022    (IN) .............................. 202221017061

(51) Int. Cl.
*C10G 1/08*    (2006.01)
*C10G 1/00*    (2006.01)
*C12P 7/10*    (2006.01)

(52) U.S. Cl.
CPC ............. *C10G 1/086* (2013.01); *C10G 1/002* (2013.01); *C12P 7/10* (2013.01); *C10G 2300/1014* (2013.01); *C10G 2400/02* (2013.01); *C10G 2400/04* (2013.01); *C10G 2400/08* (2013.01)

(58) Field of Classification Search
CPC .................... C10G 1/002; C10G 1/086; C10G 2300/1014; C10G 2400/02; C10G 2400/04; C10G 2400/08; C12P 7/10
See application file for complete search history.

(56) References Cited

FOREIGN PATENT DOCUMENTS

WO    WO-2021209555 A1 *  10/2021    ............. C10G 1/002

OTHER PUBLICATIONS

Jensen, C.U., Guerrero, J.K.R., Karatzos, S., Olofsson, G., Iversen, S.B., âFundamentals of Hydrofactionâ¢: Renewable crude oil from woody biomassâ, Biomass Conv. Bioref, 2017, 7, 495-509 (Year: 2017).*

* cited by examiner

*Primary Examiner* — James C Goloboy
(74) *Attorney, Agent, or Firm* — McDonnell Boehnen Hulbert & Berghoff LLP (57) ABSTRACT

The present invention relates to a solvothermal process for producing high quality fuels and chemicals from a biomass feedstock using lignin containing bioliquor as a solvent for hydrothermal liquefaction. The lignin containing bioliquor of the present invention is obtained as a waste stream from 2G-ethanol manufacturing plants.

19 Claims, 2 Drawing Sheets

VALUABLE CHEMICALS PRODUCTION FROM CO-LIQUEFACTION OF BIOLIQUOR AND BIOMASS

This application is a U.S. national phase of International Application No. PCT/IB2022/054956, filed on May 26, 2022, which claims priority to Indian Application No. 202221017061, filed Mar. 25, 2022, both of which are incorporated by reference herein in their entirety.

FIELD OF THE INVENTION

The present invention generally relates to a process for preparing hydrocarbons and chemicals. Specifically, the present invention relates to a solvothermal process for producing high quality fuels and valuable chemicals from a biomass feedstock using lignin containing bioliquoras a solvent for hydrothermal liquefaction along with catalyst. The lignin containing bioliquor of the present invention is produced as a waste stream from 2G-ethanol manufacturing plants.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

Emergent interest in renewable energies due to reduction in reserves of fossil fuels and climate change concerns have led to extensive research towards gaseous and liquid fuels production from renewable energy resources such as biomass and waste. Biomass has been under worldwide-study as a feedstock for preparing hydrocarbon liquid bio-fuels due to its low cost and extensive availability. Various studies on conversion of biomass into hydrocarbon liquid biofuels via hydrothermal liquefaction in laboratory scale reactors and autoclaves are under investigation.

Hydrothermal liquefaction (HTL) is a thermo-chemical depolymerization process of converting biomass into liquid fuels in the presence of solvent using elevated temperature and pressure. Hydrothermal liquefaction of lignocellulosics, including bagasse, has been investigated using different solvents and process conditions to identify the potential of bio-oil synthesis. The efficiency of HTL using various types of biomass is dependent on various process parameters such as reaction temperature, reaction pressure, solvent, biomass/solvent ratio, the type of reactor, and so on.

*Biofuel. Bioprod. Bioref.* 9:630-638 (2015) discloses hydrothermal liquefaction (HTL) of sugarcane bagasse using ethanol and black liquor as solvents. However, the oil yield is less and HTL does not utilize a catalyst.

Although there are various studies of hydrothermal liquefaction that emphasis on oil yields and products from biomass at few isolated hydrothermal liquefaction conditions, still there requires an optimisation on hydrothermal liquefaction temperatures and other parameters to achieve high yield of oils.

As alternatives to the current non-renewable energy sources like oil or natural gas, bio-fuels produced from different biomass have been explored by scientists around the world. Depending on the source, and technological impact, three generations of bio-fuels have been identified. First generation bio-fuels have been produced from food sources like sugarcane, corn, soy, through techniques like fermentation, trans-esterification and distillation and have been in use for several decades. The downside of this first generation fuels is that the feedstock is a food resource and any further technological progess in this field would lead to an imbalance in the suppy-demand of food for the world. Whereas, second generation biofuels are produced from biomass that are not a food source. For example, switch grass, corn stover, wheat straw, rice straw, rice husk, municipal waste, and so on. The advantage of using this second generation fuel manufacturing is that most of this feedstock is bio-waste and there is abundance availability of this source. In the process of production of this 2G ethanol, a waste stream of bio-liquor, rich in lignin is drawn out. Worldwide, several studies included treatment techniques to upgrade this liquor, and few of these studies also mention about the separation of lignin to be used as a combustible fuel.

Therefore, there is a need to provide a method of producing high quality fuels and valuable chemicals from biomass feedstock using bio-solvent which results in ease of conversion, energy recovery, and oil compositions, for different applications.

OBJECTS OF THE INVENTION

An object of the present invention is to provide a method of solvothermal process for producing high quality fuels and valuable chemicals from a biomass feedstock using lignin containing liquor as a solvent for hydrothermal liquefaction.

Another object of the present invention is to provide a method of solvothermal process for producing high quality fuels and chemicals from a biomass feedstock using lignin containing liquor as a solvent for liquefaction wherein the lignin containting liquor is formed from the acid/base pre-treatment of 2G-ethanol plant waste stream.

Another object of the present invention is to provide a method of solvothermal process for producing high quality fuels and chemicals from a biomass feedstock using lignin containing liquor as a solvent for hydrothermal liquefaction yielding very good oil yield with assistance of catalyst.

SUMMARY OF THE INVENTION

The present invention relates to a solvothermal process for producing high quality fuels and chemicals from a biomass feedstock using lignin containing liquor as a solvent for liquefaction. The lignin containing liquor of the present invention is produced as a waste stream from 2G-ethanol manufacturing plants.

The present invention points toward the determination that bio-liquor, a waste stream containing lignin from the 2G-ethanol plants can be made use as a solvent instead of water for the liquefaction of biomass, into useful bio-oil consisting of valuable chemicals. Furthermore, a transition-metal based oil soluble catalyst is used during the process of hydrothermal liquefaction to enhance the degradation of biomass and improve the oil yield.

In one aspect, the present invention relates to a method of producing valuable fuels and chemicals comprising the steps of:
  (a) mixing biomass feedstock in a feedstock vessel and introducing the feedstock into a hydrothermal liquefaction reactor;
  (b) processing a lignocellulose biomass in a biomass treatment unit to obtain a processed lignocellulose biomass and bioliquor and fermenting the processed lignocellulose biomass in a fermenter to obtain ethanol;

(c) introducing the bioliquor stream into the hydrothermal liquefaction reactor comprising of the feedstock to obtain a mixture;
(d) subjecting the mixture to hydrothermal liquefaction by adding a transition-metal catalyst to obtain a liquefied product;
(e) collecting the liquefied product in a collection vessel and separating the liquefied product into a gaseous product and a gas-free product stream;
(f) separating the gas-free product stream into oil stream comprising valuable fuels and chemicals, a solid phase and an aqueous phase;
(g) optionally purifying the oil stream to obtain purified oil stream; and
(h) optionally updgrading the purified oil stream to obtain fuels and chemicals.

In another embodiment of the present invention, the biomass feedstock is selected from rice straw, rice husk, saw dust, corn stover and combination thereof.

In another embodiment of the present invention, the processing of lignocellulose biomass comprises the step of treating lignocellulose biomass with acid or base and $C_5$-$C_6$ sugars.

In another embodiment of the present invention, wherein the acid is organic acid or inorganic acids, the base is sodium hydroxide or potassium hydroxide and $C_5$-$C_6$ sugar is xylose, arabinose, glucose, fructose or lignin.

In another embodiment of the present invention, the bioliquor stream comprises of sodium hydroxide and lignin.

In another embodiment of the present invention, the hydrothermal liquefaction is carried out at a temperature in the range of 120 deg C. to 400 deg C. and at a pressure in the range of 2 to 30 MPa.

In another embodiment of the present invention, the hydrothermal liquefaction is carried out at a temperature in the range of 180 deg C. to 350 deg C. and at a pressure in the range of 10 to 20 MPa.

In another embodiment of the present invention, the hydrothermal liquefaction is carried out in a time ranging from 5 minutes to 120 minutes.

In another embodiment of the present invention, the gaseous product obtained from the liquefied product is routed for heat integration with feedstock heating.

In another embodiment of the present invention, the separating of gas-free product stream comprises separating of bleed stream and make-up liquid which is connected with the bio-liquor for further processing.

In another aspect, the present invention relates to a purification of solid phase obtained from the gas-free product stream comprising the steps of:
(a) purifying the solid phase to obtain purified solid product; and
(b) sending the purified solid product to solid char upgradation unit to obtain a final product.

In another aspect, the present invention relates to a method of upgradation of oil stream, wherein the method of upgradation is selected from:
(a) mixing the oil stream with petroleum fractions in co-processing unit to obtain the hydrocarbons;
(b) hydrotreating the oil stream in a hydrotreating unit to obtain diesel or jet range fuels;
(c) cracking the oil stream using a fluid catalytic cracking unit in present of a catalyst in presence of a catalyst to obtain light olefins and gasoline additive compounds; and
(d) cracking the oil stream using a steam cracking unit to ethylene and propylene.

In another embodiment of the present invention, the catalyst used in the fluid catalytic cracking unit is selected from ZSM-5, beta zeolite, y-zeolite or combination thereof.

Various objects, features, aspects and advantages of the inventive subject matter will become more apparent from the following detailed description of preferred embodiments.

DETAILED DESCRIPTION OF THE INVENTION

The following is a detailed description of embodiments of the disclosure. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

Unless the context requires otherwise, throughout the specification which follow, the word "comprise" and variations thereof, such as, "comprises" and "comprising" are to be construed in an open, inclusive sense that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

The recitation of ranges of values herein is merely intended to serve as a shorthand method of referring individually to each separate value falling within the range. Unless otherwise indicated herein, each individual value is incorporated into the specification as if it were individually recited herein.

All processes described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The headings and abstract of the invention provided herein are for convenience only and do not interpret the scope or meaning of the embodiments.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C. or D, even if not explicitly disclosed.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description that follows, and the embodiments described herein, is provided by way of illustration of an example, or examples, of particular embodiments of the principles and aspects of the present disclosure. These examples are provided for the purposes of explanation, and not of limitation, of those principles and of the disclosure.

It should also be appreciated that the present invention can be implemented in numerous ways, including as a system, a method or a device. In this specification, these implementations, or any other form that the invention may take, may be referred to as processes. In general, the order of the steps of the disclosed processes may be altered within the scope of the invention.

Various terms as used herein are shown below. To the extent a term used in a claim is not defined below, it should be given the broadest definition persons in the pertinent art have given that term as reflected in printed publications and issued patents at the time of filing.

The term. "hydrothermal liquefaction reactor" as used herein refers to a reactor in which a solvent is used at its super critical conditions for hydrothermal liquefaction to convert any organic substance to crude oil and chemicals at moderate temperature and pressure. Generally, the hydrothermal liquefaction process is conducted in a batch type autoclave reactor, that can sustain temperatures unto 500 deg C. and pressures unto 32 MPa, fitted with an electrically heated furnace, high temperature thermocouple, stirrer, and pressure gauge. The reactor material can be stainless steel (SS316) and the volume of reactor is anywhere between 0.5 to 1.2 L. The reactor used in this study was a 0.5 L high temperature and high pressure stirred reactor (Parr 4575) with Parr 4848B reactor controller obtained from Parr Instrument Co., Moline, IL, US.

The term "transition metal catalyst" as used herein refers to a catalyst as prepared in the patent applications, US20210339235A1 and WO2018235094A1. The transition metal catalyst can be oil soluble catalyst or water soluble catalyst and in the form of powder.

In a general embodiment, the present invention relates to a solvothermal process for producing high quality fuels and chemicals from a feedstock of biomass using lignin containing bioliquor as a solvent for hydrothermal liquefaction. The lignin containing bioliquor of the present invention can be obtained as a waste stream from 2G-ethanol manufacturing plants.

In first embodiment, the present invention relates to a method of producing fuels and chemicals comprising the steps of:
(a) mixing biomass feedstock in a feedstock vessel and introducing the feedstock into a hydrothermal liquefaction reactor,
(b) processing a lignocellulose biomass in a biomass treatment unit to obtain a processed lignocellulose biomass and bioliquor and fermenting the processed lignocellulose biomass in a fermenter to obtain ethanol,
(c) introducing the bioliquor stream into the hydrothermal liquefaction reactor comprising of the feedstock to obtain a mixture;
(d) subjecting the mixture to hydrothermal liquefaction by adding a transition-metal catalyst to obtain a liquefied product;
(e) collecting the liquefied product in a collection vessel and separating the liquefied product into a gaseous product and a gas-free product stream;
(f) separating the gas-free product stream into oil stream comprising fuels and chemicals, a solid phase and an aqueous phase;
(g) optionally purifying the oil stream to obtain purified oil stream; and
(h) optionally updgrading the purified oil stream to obtain fuels and chemicals.

Figure 1:
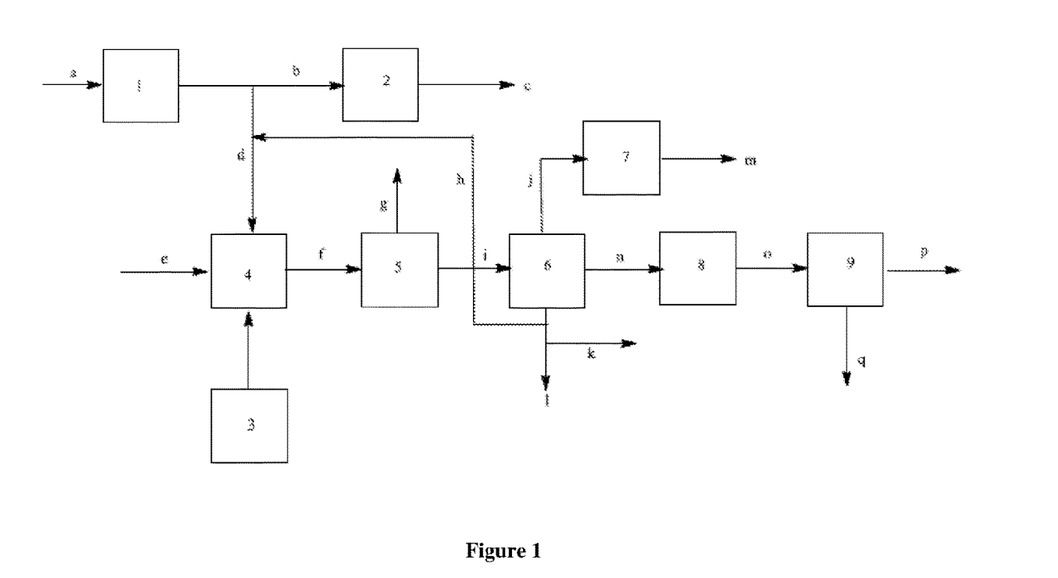
FIG. 1 represents process flow for the catalytic hydrothermal liquefaction of biomass feedstock using bio-liquor as a solvent.

In another embodiment of the present invention, the FIG. 1 shows the flow scheme for the catalytic hydrothermal liquefaction of biomass in the presence of solvent and a transition metal catalyst to obtain valuable chemicals and fuels in accordance with the present disclosure. According to the present invention, the feedstock of biomass is stored or mixed in the feed hopper combined with feeder, feedstock vessel (3). The biomass feedstock is introduced into the hydrothermal liquefaction reactor (HTL) reactor (4). The lignocellulosic biomass is initially processed in the biomass pre-treatment unit (1) where acid/base pre-treatment occurs and then, the $C_5$-$C_6$ sugars (b), constituting cellulose and hemicellulose are sent into a fermenter (2), where the ethanol (c) is the main product along with a lignin containing liquor stream (d). This bio-liquor(d) is composed of sodium hydroxide and lignin. The bio-liquor stream (d) is sent to a HTL reactor (4). A transition-metal catalyst (e) is added to the fresh biomass feed (10-20 wt % in solvent) in the HTL reactor. The hydrothermal liquefaction takes place at a temperature in the range of 120 deg C. to 400 deg C. and at a pressure in the range of 2 to 30 MPa, and for a residence time 5 min to 120 min to obtain a liquefied product stream (mixture of solid char, aqueous phase and oil phase) (f). This liquefied product stream (f, obtained during the hydrothermal liquefaction is sent into a product collector vessel (5), where the gaseous product (g) can be collected, sent to vent, or routed for heat integration with feedstock heating. The gas-free product stream (i) is sent into a liquid-solid separator (6), where the gas-free product stream can be subjected to a single stage or multi-stage separation procedures. The bio crude stream (j) is separated from the solid phase (n) and the aqueous phase (k). A bleed stream (l) and make-up liquid (h) are also separated.

In another embodiment of the present invention, the oil phase j) can be purified or processed in (7) and final oil (m) can be sent for upgradation or blending into drop in fuel/co-processed in refinery units like fluid catalytic cracking or hydrocracking/hydrotreater.

In another embodiment of the present invention, the solid phase (n) is sent into a purification unit (8), where the solid phases is purified and sent into an solid char upgradation unit (9) to a final product which can be used as a catalyst support (p) or for bio-remediation aid(q). The solid char upgradation unit can use steam, KOH or any other activation agent for improving surface area and physical properties of raw char stream (o).

In an embodiment of the present invention, the make-up liquid (h) can be integrated with the bio-liquor stream.

In an embodiment of the present invention, the biomass for feedstock is selected from any of the different kinds of lignocellulosic biomass categories—hardwood, softwood, grasses and agricultural wastes. Examples of such biomass are poplar, oak, *eucalyptus*, pine, douglas fir, spruce, wheat straw, barley hull, barley straw, rice straw, rice husks, oat straw, ray straw, corn cobs, corn stalks, sugarcane bagasse, sorghum straw, grass, switch grass and so on or combination thereof. Preferably, the biomass for feedstock is rice straw, rice husk, saw dust, corn stover or combination thereof.

In an embodiment of the present invention, the bioliquor stream can be formed from the acid/base pre-treatment of 2G-ethanol plant waste stream, as a solvent for the process, that aids in improving the bio crude oil yield and in producing aromatics having $C_8$-$C_{13}$ carbons that are useful in the gasoline pool as research octane number (RON) improvement additives.

In an embodiment of the present invention, the biomass used for the preparation of bioliquor can be selected from perennial grasses (*miscanthus giganteus*, switch grass), poplar tree, willow tree, or wastes like rice straw, corn stover, wheat straw, and so on.

In an embodiment of the present invention, the biomass solids loading is present in a concentration range of 10-30 wt %.

In an embodiment of the present invention, the transition-metal based oil-soluble catalyst or powdered catalyst is in the concentration of 0.1-10 wt % of solids loading for enhancing the quality of the fuel oils and lubricating oils.

In another embodiment of the present invention, the transition-metal catalyst can be Fe. Mo, Ni, or Co based catalyst or iron powder, Ni powder, or high Fe containing red mud powder catalyst.

In an embodiment of the present invention, the bio-liquor stream comprises of 1% to 10 wt % sodium hydroxide (NaOH) and lignin about 1 to 40 wt % and can be associated with lignin concentration step using multi effect evaporation to obtain high concentration of lignin.

In an embodiment of the present invention, the hydrothermal liquefaction takes place at a temperature in the range of 120 deg C. to 400 deg C. Preferably, at a temperature in the range of 180 deg C. to 350 deg C. More preferably, at a temperature in the range of 300 deg C. to 350 deg C.

In an embodiment of the present invention, the hydrothermal liquefaction takes place at a pressure in the range of 2 to 30 MPa. Preferably, at a pressure in the range of 15 to 25 MPa. More preferably, at a pressure in the range of 20 to 25 MPa.

In another embodiment of the present invention, the hydrothermal liquefaction reaction is carried out in a time ranging from 5 minutes to 120 minutes. Preferably, in a time ranging from 10 minutes to 60 minutes. More preferably, in a time ranging from 10 minutes to 20 minutes.

In an embodiment of the present invention, the catalyst used in the liquefaction can be present in the concentration range of 0.1-10 wt % of solids loading for enhancing the quality of the bio crude towards fuel oils and lubricating oils.

According to the present invention, the method of converting biomass feedstock to fuels and chemicals provides oil stream in range of 40% to 60% yield.

In another embodiment of the present invention, the oil stream generated in the present method can have higher heating value (HHV) in the range of 25-40 MJ/Kg.

In an embodiment of the present invention, the method of converting biomass feedstock to fuels and chemicals produces valuable fuel compounds, olefins and aromatics. More preferably, the aromatic group of chemical compounds.

In another embodiment of the present invention, the method of converting biomass feedstock to fuels and chemicals produces valuable compounds such as alcohol, alkenes, aromatic, cycloalkane, ketonic, and phenolic compounds.

In an embodiment of the present invention, the method of converting biomass feedstock to fuels and chemicals produces aromatics specifically in the range of $C_8$ to $C_3$. Furthermore, this process also assists in the formation of specialty chemicals such as xylene, ethyl benzene, and the like.

In an embodiment of the present invention, the method of converting biomass feedstock to fuels and chemicals produces aromatic compounds significantly in higher quantity.

In another aspect, the present invention relates to a method of upgrading the crude oil stream, wherein the method of upgrading is selected from:
  (a) mixing the oil stream with petroleum fractions in co-processing unit to obtain the hydrocarbons;
  (b) hydrotreating the oil stream in a hydrotreating unit to obtain diesel or jet range fuels;
  (c) cracking the oil stream using a fluid catalytic cracking unit in present of a catalyst in presence of a catalyst to obtain light olefins and gasoline additive compounds; and
  (d) cracking the oil stream using a steam cracking unit to ethylene and propylene.

Figure 2:
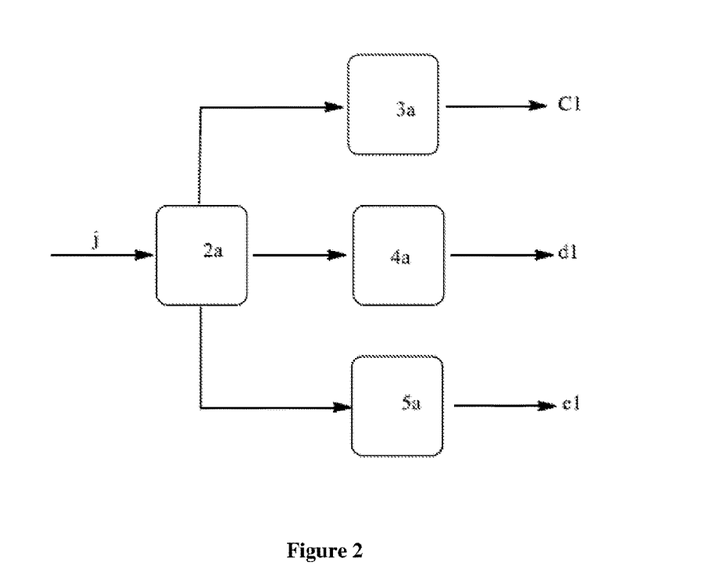
FIG. 2 represents process flow for upgradation of oil stream to valuable chemicals.

According to the present invention, FIG. 2 shows the flow scheme of upgradation techniques for the products obtained from the hydrothermal liquefaction of biomass in the presence of bio-liquor solvent. The oil stream (j) can be purified or processed in unit (2*a*). Unit (2*a*) can be a coprocessing unit, where the oil stream mixed with petroleum fractions like vacuum gas oil and heavy gas oil and processed to obtain the upgraded fuels or chemicals. Also, unit (2*a*) can be a hydrotreating unit for converting bio crude into diesel/jet range fuels. Unit (2*a*) can also be a fluid catalytic cracking unit, where bio crude can be cracked in presence of catalysts like zeolites (ZSM-5, beta-zeolite, y-zeolite etc) to light olefins and gasoline additive compounds. Unit (2a) can also be a steam cracking unit, where oil stream can be steam cracked to produce ethylene and propylene.

In another embodiment of the present invention, the updgradation of oil stream (j) comprising the step of:
(a) purifying oil stream (J) in unit (2a) to obtain purified oil stream; and
(b) carrying out phenolic compounds purification in unit (3a) to obtain purified phenolic rich stream (c1).

In an embodiment of the present invention, the updgradation of oil stream (j) comprising the step of;
(c) purifying oil stream (j) in unit (2a) to obtain purified oil stream, and
(d) carrying out aromatics purification in unit (4a) to obtain purified $C_8$-$C_{15}$ rich aromatic stream (dl).

In an embodiment of the present invention, the updgradation of oil stream (j) comprising the step of:
(a) purifying oil stream (j) in unit (2a) to obtain purified oil stream; and
(b) carrying out paraffns purification in unit (5a) to obtain paraffin stream (el).

While the foregoing describes various embodiments of the disclosure, other and further embodiments of the disclosure may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

EXAMPLES

The present invention is further explained in the form of following examples. However, it is to be understood that the following examples are merely illustrative and are not to be taken as limitations upon the scope of the invention.

The biomass used in the present invention is procured from the local animal feed market in Devangonthy, Bengaluru.

Preparation 1—Bioliquorsolvent Preparation

Bio-liquor is produced as a waste stream from the 2G-ethanol plants. This is further sent for treatment so as to concentrate the lignin content in the stream.

Sulfuric acid (2 g) is taken for about 100-200 ml of untreated bioliquor. This solution is made up to 500-600 ml using water. Around 100-150 g biomass (Rice starw) is added to this solution and is soaked for 30 min to 1 hour. The soaked liquor is then cooked in a reactor for 15 to 30 min at a temperature of 100-200 deg C. Later, after it cools down, residue is squeezed manually, and the waste liquor of about 300 to 400 ml is produced which is disposed. Now, the solid residue which is containing about 100 to 200 ml liquor is taken, and to this, about 2% sodium hydroxide solution is added. For 1 eq of the solid residue, an equal amount of sodium hydroxide solution is added and left for some time. Further, the process of manual squeezing is done so as to neutralize the solid residue, and bring down its moisture content to below 100 g. Now, a 3% solution is prepared and 200 to 300 ml sodium hydroxide is added to it. This solution is then cooked for 30 min to 1 hour at a temperature of 100-200 deg C. to get a final bio-liquor solution.

The bio-liquor solution obtinaed is used as a low cost fuel, but, in this innovation, it is being used as a solvent for the hydrothermal liquefaction of biomass, as the lignin content in the liquor aids in forming very useful bio-crude oil, that can be further used as a diesel or gasoline blend.

Preparation 2—Synthesis of Transition-Metal Catalyst

For the metal precursor, about 100 g molybdic acid is taken and a solution is prepared. To this, 100 g of 2-ethyl hexanoic acid (first additive) solution was added and refluxed at 180° C. for 4 hours to obtain the dark black color salt. The salt was cooled and re-dissolved in 150 g of 2-ethyl hexanol (second additive) and heated with reflux at 180° C. for 12 hours to obtain the Mo(O),(2-ethyl hexanoate)2-ethyl hexanolate catalyst. About 340 g was produced with the Mo percentage around 14%.

Preparation 3—Synthesis of Transition-Metal Catalyst

To a solution of iron (111) nitrate (1 eq.) in water and hexane (1:2 ratio; 5 ml per 1 mmol of Fe salt), sodium 2-ethyl hexanoate (3 eq.) in water (solution of 1 mmol in 1 mL water) was added drop wise at 70° C. and the solution was refluxed for 3 h at 80° C. The resulting reaction mixture was cooled and fractionated between water/hexane layers. The organic layer was washed with the water. The organic phase was dried ($Na_2NO_3$), concentrated in vacuo to afford the catalyst, iron ethyl-hexanoate as a gummy solid.

Example 1

Solvothermal liquefaction of biomass as feedin presence of lignin containing liquor solvent and molybdenum oil-soluble catalyst were performed in a high pressure and high temperature 500 mL autoclave (Parr 4848B model, USA) equipped with a pressure sensor, J-type thermocouple and an external electric furnace, where the heating system is controlled by a PID controller 20 g of biomass feedstock, lignin containing bio-liquor solvent (80 g) and 0.2 g of Molybdenum oil-soluble catalyst are loaded into the reactor. The reactor was purged with nitrogen gas to maintain an inert homogeneous atmosphere. A pressure test was carried out to ensure the reactors and lines are securely sealed and no leak was observed. Initial pressure of the reactor was kept at atmospheric pressure, and stirrer speed was adjusted to 350 rpm. Reactor was then allowed to reach the desired reaction temperature of 593 deg K with increments of 10 deg K/min. Once the temperature is reached, the reactor is kept at the desired temperature for residence time of 15 minutes at the pressures of 23-25 MPa. On the completion of the reaction, the autoclave is immediately cooled to room temperature with an external cooling bath. After the gas samples were collected for analysis using gas bags, the pressure was released from the reactor through vent. For the separation process, the contents of the reactor and the stirrer are washed thoroughly with a solvent ethylacetate several times. The mixture was filtered with the help of buchner filter funnel, to remove the solids from the liquid phase. Two layers are observed in the separating funnel, where the oil stream is separated from the aqueous stream. Oil stream is extracted from the liquid samples by separating the solvent in a rotary vacuum evaporator (Buchi Rotavapor). The compounds obtained in the oil stream is given in the table 1 and 1a below.

TABLE 1

Example 1-List of all major compounds
Biomass (Rice Husk) + 80 g BL + Mo Catalyst

| Area % | Compound (All compounds) |
|---|---|
| 7.04 | 11-Methyldodecanol |
| 5.54 | Phenol, 2-methyl- |

TABLE 1-continued

Example 1-List of all major compounds
Biomass (Rice Husk) + 80 g BL + Mo Catalyst

| Area % | Compound (All compounds) |
|---|---|
| 4.9 | 2,4-Dimethyl-1-heptene |
| 4.71 | o-Cymene |
| 4.53 | Phenol, 2-ethyl-4-methyl- |
| 4.32 | Cyclohexane, 1,1-dimethyl-2-propyl- |
| 4.09 | Ethanone, 1-(1-cyclohexen-1-yl)- |
| 4.05 | Phenol |
| 4.03 | 2-Cyclopenten-1-one, 2,3-dimethyl- |
| 3.8 | Phenol, 3,5-dimethyl- |
| 3.36 | 2-Cyclopenten-1-one, 2,3,4-trimethyl- |
| 2.93 | o-Xylene |
| 2.9 | p-Cresol |
| 2.85 | Cyclopentane, 1-acetyl-1,2-epoxy- |
| 2.75 | Ethylbenzene |
| 2.7 | Phenol, 2,6-dimethyl- |
| 2.58 | Phenol, 4-ethyl- |
| 2.27 | Cyclohexanone |
| 2.25 | Cyclobutane, 1-butyl-2-ethyl- |
| 2.18 | Undecane, 4,6-dimethyl- |
| 2.15 | Cyclohexane, 1,3,5-trimethyl- |
| 2.02 | 5,8-Decadien-2-one, 5,9-dimethyl-, (E)- |
| 1.94 | 2,4-Pentadien-1-ol, 3-pentyl-, (2Z)- |
| 1.92 | 2-Heptene, (E)- |
| 1.85 | 1-Tricosene |
| 1.82 | 1-Octanol, 3,7-dimethyl- |
| 1.81 | 3-Octadecene, (E)- |
| 1.79 | [2-(2,2-Dimethyl-tetrahydro-pyran-4-yl)-ethyl]-(4-methoxy-benzyl)-amine |
| 1.79 | 1-Decanol, 2-hexyl- |
| 1.77 | Phenol, 2-methoxy- |
| 1.54 | Thymol |
| 1.52 | 2-Octen-1-ol, 3,7-dimethyl- |
| 1.45 | Cyclopentane, 1,2,3,4,5-pentamethyl- |
| 1.45 | cis-4-Decenal |
| 1.43 | Phenol, 2,4,6-trimethyl- |

TABLE 1a

Example 1-List of all major chemical group compounds
Example 1: Biomass (Rice Husk) + 80 g BL +
Mo Catalyst (Functional compounds)

| Compounds | Area % |
|---|---|
| Alcohol | 14.11 |
| Alkenes | 10.48 |
| Aromatic | 13.29 |
| Cycloalkane | 13.02 |
| Ketonic | 15.77 |
| Phenolic | 27.94 |
| Others | 5.42 |

The following examples and comparative examples were produced using the above experimental procedures with appropriate conditions, and starting material as given in the table below with non-critical variations.

Example 2

TABLE 2

List of all major compounds
Example 2: Rice Straw + 80 g BL + Mo Catalyst

| Area % | Compound |
|---|---|
| 1.37 | Cyclohexanol, 5-methyl-2-(1-methylethyl)-, [1S-(1.alpha.,2.alpha.,5.beta.)]- |
| 1.55 | Tridecane |
| 3.33 | Tetradecane |
| 1.77 | Heptadecane |
| 1.25 | Octadecane |
| 2.04 | Hexadecane |
| 0.86 | Heptadecane |
| 1.26 | 1-Methylcyclooctene |
| 17.51 | p-Xylene |
| 3.44 | Benzene, 1-ethyl-2-methyl- |
| 2.06 | Mesitylene |
| 4.14 | Benzene, 1-ethyl-3-methyl- |
| 10.74 | Mesitylene |
| 3.11 | Benzene, 1,2,3-trimethyl- |
| 1.34 | p-Cymene |
| 1.27 | Benzene, 1-ethyl-3,5-dimethyl- |
| 0.76 | Naphthalene |
| 1.67 | Benzene, 1-ethyl-4-methoxy- |
| 1.37 | Cyclohexane, (1-methylethylidene)- |
| 1.33 | Indane |
| 1.52 | 2-Cyclopenten-1-one, 3,4-dimethyl- |
| 1.36 | 2-Cyclopenten-1-one, 3-methyl- |
| 3.83 | 2-Cyclopenten-1-one, 2,3-dimethyl- |
| 2.01 | Ethanone, 1-(1-cyclohexen-1-yl)- |
| 2.2 | Phenol, 2-methoxy- |
| 2.2 | Phenol, 2-methoxy- |
| 9.93 | Phenol |
| 1.46 | Phenol, 4-ethyl- |
| 5.14 | Phenol, 2-ethyl- |
| 1.56 | Phenol, 3-methyl- |
| 2.9 | Phenol, 3-ethyl-5-methyl- |
| 3.71 | Phenol, 3-ethyl- |

TABLE 2a

List of all major chemical group compounds
Example 2: Rice Straw + 80 g BL Mo Catalyst

| Compounds | Area % |
|---|---|
| Aromatic | 46.04 |
| Alcohol | 1.37 |
| Alkane | 10.8 |
| Alkene | 1.26 |
| Cycloalkane | 2.70 |
| Ketonic | 8.72 |
| Phenolic | 29.10 |

Comparative Example 1 (CE-1)

TABLE 3

List of all major compounds
CE-1: Rice Husk + 80 g BL Without Catalyst

| Area % | Compound |
|---|---|
| 17.99 | o-Cymene |
| 5.7 | o-Xylene |
| 5.11 | 2-Cyclopenten-1-one, 2,3-dimethyl- |
| 3.63 | 1-Penten-3-one, 1-(2,6,6-trimethyl-2-cyclohexen-1-yl)-, (E)- |
| 3.61 | 1H-Indene, 2,3-dihydro-1,6-dimethyl- |
| 3.53 | Phenol, 2-methyl- |
| 3.41 | Naphthalene, 2,3,6-trimethyl- |
| 3.27 | Benzene, 1-methyl-4-(1-methyl-2-propenyl)- |
| 2.73 | Phenol, 3,4-dimethyl- |
| 2.34 | 1H-Indene, 2,3-dihydro-4-methyl- |
| 2.33 | 2,5-cyclohexadiene-1,4-dione, 2,6-bis(1,1-dimethylpropyl)- |
| 2.29 | Benzene, (2-methyl-1-butenyl)- |
| 2.27 | Benzene, 1-ethyl-2-methyl- |

TABLE 3-continued

List of all major compounds
CE-1: Rice Husk + 80 g BL Without Catalyst

| Area % | Compound |
|---|---|
| 2.27 | 2-Phenyl-4-penten-2-ol |
| 2.24 | Dodecane, 1-(heptylthio)- |
| 2.22 | 5-Hexen-2-one, 5-methyl-3-methylene- |
| 2.17 | 2-Cyclopenten-1-one, 2,3,4-trimethyl- |
| 2.16 | Cyclobutene, 1,2,3,4-tetramethyl- |
| 2.16 | Phenol, 4-ethyl- |
| 2.15 | Cyclopentanone, 2-ethyl- |
| 2.11 | 1H-Indene, 1,1,3-trimethyl- |
| 2.08 | Benzene, (2,2-dimethyl-1-methylenepropyl)- |
| 2.01 | Benzene, 1,2,4-trimethyl- |
| 1.99 | Phenol, 2,3,5,6-tetramethyl- |
| 1.91 | Benzene, 1,2,3-trimethyl- |
| 1.89 | Ergosterol |
| 1.86 | Phenol |
| 1.84 | Cyclohexanol, 5-methyl-2-(1-methylethyl)-, (1.alpha.,2.beta.,5.alpha.)-(.+/−.)- |
| 1.83 | Phenol, 2,4,6-trimethyl- |
| 1.82 | Cyclohexene, 3,5-dimethyl- |
| 1.81 | Ylangenol |
| 1.8 | 1H-Indene, 2,3-dihydro-1,1,5-trimethyl- |
| 1.75 | Phenol, 3-(1-methylethyl)- |
| 1.73 | Benzene, 1-methyl-4-(1-methylpropyl)- |

TABLE 3a

List of all major chemical group compounds
CE-1: Rice Husk + 80 g BL Without Catalyst

| Compounds | Area % |
|---|---|
| Alcohol | 5.54 |
| Alkenes | 13.84 |
| Aromatic | 42.66 |
| Ketonic | 17.61 |
| Phenolic | 18.12 |
| Others | 2.24 |

Comparative Example 2 (CE-2)

TABLE 4

List of all major compounds
CE-2: Rice Husk + 80 g Water Without Catalyst

| Area % | Compound |
|---|---|
| 20.65 | Cyclopentane, (2-methylpropyl)- |
| 9.6 | Cyclohexane, 1,2-dimethyl-, trans- |
| 7.99 | 3-Octyne |
| 6.45 | Cyclohexene,3-propyl- |
| 5.37 | Cyclohexane, 1,3-dimethyl-, trans- |
| 4.49 | Phenol, 4-ethyl- |
| 4.45 | 1-Hexanol, 2-ethyl- |
| 4.38 | Cyclopentane, (1-methylethyl)- |
| 3.71 | Cyclodecane, octyl- |
| 3.01 | p-Cresol |
| 2.9 | 2-Cyclopenten-1-one, 2,3-dimethyl- |
| 2.5 | Bicyclo[2.2.1]heptane, 2-methyl-, exo- |
| 2.49 | Phenol, 2-methyl- |
| 2.43 | Phenol, 3-methyl- |
| 2.26 | Cycloheptane, methyl- |
| 1.78 | Cyclopentane, 1-ethyl-2-methyl-, cis- |
| 1.75 | 2-Cyclopenten-1-one, 3-methyl- |
| 1.75 | 3-Hexanol, 3-methyl- |
| 1.41 | Cyclopropane, pentamethyl- |
| 1.41 | Cyclopentane, 1-ethyl-1-methyl- |
| 1.29 | 3-Undecene, 5-methyl- |
| 1.16 | Phenol, 2,4-dimethyl- |
| 1.15 | 2-Octene, 2,3,7-trimethyl- |

TABLE 4-continued

List of all major compounds
CE-2: Rice Husk + 80 g Water Without Catalyst

| Area % | Compound |
|---|---|
| 1.11 | Benzene, 1,3-dimethyl- |
| 1.11 | Phenol, 3,4-dimethyl- |
| 1.04 | Cyclohexane, 1-ethenyl-2-methyl-, trans- |
| 0.84 | 2-Hepten-4-one, 2-methyl- |
| 0.79 | Phenol, 2-ethyl- |
| 0.74 | p-Cumenol |

TABLE 4a

List of all major chemical group compounds
Rice Husk + 80 g Water Without Catalyst

| Compounds | Area % |
|---|---|
| Alcohol | 6.2 |
| Alkenes | 2.44 |
| Alkynes | 7.99 |
| Aromatic | 4.86 |
| Cycloalkane | 54.11 |
| Ketonic | 5.49 |
| Phenolic | 12.47 |

Comparative Example—3 (CE-3)

TABLE 5

List of all major compounds
CE:3 Rice Husk + 80 g Water Mo Catalyst

| Area % | Compound |
|---|---|
| 24.27 | Hexanoic acid, 2-ethyl- |
| 5.97 | Naphthalene, 2-methyl- |
| 5.32 | Phenol |
| 5.23 | Phenol, 4-ethyl- |
| 5.21 | p-Cresol |
| 4.55 | 1-Phenyl-1-butene |
| 3.71 | 2-Hexene, 4,4,5-trimethyl- |
| 3.63 | Naphthalene, 1-methyl- |
| 3.56 | Phenol, 2-methyl- |
| 3.32 | 2-Cyclopenten-1-one, 2,3-dimethyl- |
| 3.01 | Naphthalene, 2,6-dimethyl- |
| 2.74 | Naphthalene, 1,6-dimethyl- |
| 2.67 | Naphthalene |
| 2.45 | 1H-Indene, 2,3-dihydro-5-methyl- |
| 2.31 | Phenol, 3,5-dimethyl- |
| 1.99 | 1,1'-Bicyclohexyl |
| 1.92 | Mesitylene |
| 1.81 | p-Xylene |
| 1.76 | ±trans-1-Isopropenyl-4-methyl-1,4-cyclohexanediol |
| 1.73 | Benzene, 1-(1-methylethenyl)-4-(1-methylethyl)- |
| 1.54 | 2-Cyclopenten-1-one, 2-methyl- |
| 1.49 | 1H-Indene, 2,3-dihydro-4,7-dimethyl- |
| 1.45 | Naphthalene, 2-(1-methylethyl)- |
| 1.37 | Ethylbenzene |
| 1.24 | Benzene, 1,2,3,4-tetramethyl- |
| 1.19 | Cyclohexane, 1,3,5-trimethyl-, (1.alpha.,3.alpha.,5.beta.)- |
| 1.16 | 2,4-Dimethyl-1-heptene |
| 1.16 | Naphthalene, 1,3-dimethyl- |
| 1.12 | Cyclohexane, 1,3,5-trimethyl- |
| 1.11 | Cyclohexanone |

TABLE 5a

List of all major chemical group compounds
CE:3 Rice Husk + 80 g Water Mo Catalyst

| Compounds | Area % |
|---|---|
| Alcohol | 1.76 |
| Alkenes | 6.36 |
| Saturated fatty acid | 24.27 |
| Aromatic | 28.7 |
| Cycloalkane | 3.18 |
| Ketonic | 4.86 |
| Phenolic | 26.18 |
| Others | 4.68 |

Comparative Example 4 (CE-4)

TABLE 4

List of all major compounds
CE-4: Rice Straw + 80 g BL Without Catalyst

| Area % | Compound |
|---|---|
| 0.8 | 1-Octanol, 2-butyl- |
| 0.72 | 2-Tetradecanol |
| 0.83 | Heptadecane |
| 1.37 | 3-Undecene, 5-methyl- |
| 1.27 | 2-Decene, 2,4-dimethyl- |
| 5.41 | o-Cymene |
| 2.3 | o-Xylene |
| 1.52 | Benzene, 1-ethyl-2-methyl- |
| 1.11 | Ethylbenzene |
| 12.01 | Oleic Acid |
| 5.19 | n-Hexadecanoic acid |
| 5.1 | Hexadecanoic acid, 2-(octadecyloxy)ethyl ester |
| 2.01 | Heptanoic acid, docosyl ester |
| 1.19 | Cyclohexene, 3,3,5-trimethyl- |
| 1.04 | Cyclopentane, 1-acetyl-1,2-epoxy- |
| 0.97 | Cyclooctane, ethenyl- |
| 3.45 | 5-Hexen-2-one, 5-methyl-3-methylene- |
| 3.26 | 2-Cyclopenten-1-one, 2,3-dimethyl- |
| 1.43 | 2-Cyclopenten-1-one, 2,3,4-trimethyl- |
| 0.79 | Cyclohexanone |
| 1.6 | 1H-Pyrrole, 3,4-diethyl-2-methyl- |
| 1.15 | D-Limonene |
| 0.92 | 1H-Pyrrole, 2,3,4,5-tetramethyl- |
| 2.75 | Phenol, 2,4-dimethyl- |
| 2.34 | Phenol |
| 2.25 | Phenol, 2-methyl- |
| 2.02 | Phenol, 2,3,5,6-tetramethyl- |
| 1.85 | Phenol, 2-(1-methylethyl)-, methylcarbamate |
| 1.74 | Phenol, 4-ethyl- |
| 0.97 | Phenol, 2,6-dimethyl- |
| 0.89 | Thymol |
| 0.66 | Phenol, 3-ethyl-5-methyl- |

List of all major chemical group compounds

Rice Husk + 80 g Water Without Catalyst

| Compounds | Area % |
|---|---|
| Aromatic | 10.34 |
| Alcohol | 1.52 |
| Alkane | 0 |
| Alkene | 2.64 |
| Cycloalkane | 0 |
| Ketonic | 8.93 |
| Phenolic | 15.47 |
| Fatty acid | 24.31 |
| Others | 4.50 |

Comparative Example 5 (CE-5)

TABLE 5

List of all major compounds
CE-5: Rice Straw + 80g Water Mo Catalyst

| Area % | Compound |
|---|---|
| 2.19 | 2.4-Hexadiene, 2,3-dimethyl- |
| 2.05 | Ethylbenzene |
| 6.06 | Acetophenone |
| 2 | Cyclohexane, (1-methylethylidene)- |
| 3.31 | Cyclohexane, (1-methylethylidene)- |
| 2.41 | 2-Cyclopenten-1-one, 2-methyl- |
| 2.55 | 2-Cyclopenten-1-one, 3-methyl- |
| 2.18 | 2-Cyclopenten-1-one, 3,4-dimethyl- |
| 1.16 | 2-Cyclopenten-1-one, 3,4-dimethyl- |
| 6.99 | 2-Cyclopenten-1-one, 2,3-dimethyl- |
| 5.98 | Ethanone, 1-(1-cyclohexen-1-yl)- |
| 1.47 | Cyclopentanone, 2-methyl- |
| 3.14 | Hexanoic acid, 2-ethyl- |
| 9.55 | Phenol |
| 7.82 | Phenol, 2-methyl- |
| 8.2 | Phenol, 3-methyl- |
| 3.07 | Phenol, 2-ethyl- |
| 1.91 | Phenol, 2,4-dimethyl- |
| 2.21 | Phenol, 2,6-dimethyl- |
| 10.97 | Phenol, 4-ethyl- |
| 1.29 | 2-Ethylphenol, methyl ether |
| 1.75 | Phenol, 3-(1-methylethyl)- |
| 1.32 | Phenol, 2,4,5-trimethyl- |
| 3.41 | Phenol, 2-(1-methylethyl)-, methylcarbamate |
| 1.59 | Phenol, 2-propyl- |
| 1.71 | Phenol, 4-ethyl-2-methoxy- |
| 2.54 | Phenol, 2,3,5,6-tetramethyl- |
| 1.18 | Biphenyl |

TABLE 5a

List of all major chemical group compounds
Rice Straw + 80 g Water Mo Catalyst

| Compounds | Area % |
|---|---|
| Aromatic | 8.11 |
| Alcohol | 0 |
| Alkane | 0 |
| Alkene | 2.19 |
| Cycloalkane | 5.31 |
| Ketonic | 21.27 |
| Phenolic | 58.52 |
| Fatty acid | 0 |
| Others | 4.61 |

Comparative Example 6 (CE-6)

TABLE 6

List of all major compounds
CE-6: Rice Straw + 80 g Water Without Catalyst

| Area % | Compound |
|---|---|
| 2.41 | 1-Hexanol, 2-ethyl- |
| 0.83 | 3-Undecene, 5-methyl- |
| 0.79 | 3-Undecene, 5-methyl- |
| 0.45 | 8-Heptadecene, 1-chloro- |
| 0.88 | o-Xylene |
| 2.75 | p-Cresol |
| 0.52 | Benzenemethanol, .alpha.-(phosphinomethyl)- |
| 1.5 | Cyclopropane, pentamethyl- |
| 1.38 | Cyclopentane, 1-ethyl-1-methyl- |
| 5.39 | Cyclohexane, 1,3-dimethyl-, trans- |

TABLE 6-continued

List of all major compounds
CE-6: Rice Straw + 80 g Water Without Catalyst

| Area % | Compound |
|---|---|
| 8.2 | Cyclohexane, 1,4-dimethyl-, trans- |
| 4.12 | Cyclopentane, (1-methylethyl)- |
| 2.32 | Bicyclo[2.2.1]heptane, 2-methyl-, exo- |
| 2.31 | Cyclopentane, 1-ethyl-2-methyl-, cis- |
| 1.86 | Cycloheptane, methyl- |
| 13.71 | Cyclopentane, (2-methylpropyl)- |
| 1.82 | Cyclohexane, 1-ethenyl-2-methyl-, trans- |
| 1.67 | Cyclohexanone |
| 1.61 | 2-Hepten-4-one, 2-methyl- |
| 0.54 | Cyclopentanone, 2-ethyl- |
| 1.79 | 2-Cyclopenten-1-one, 3-methyl- |
| 0.81 | 2-Cyclopenten-1-one, 3,4-dimethyl- |
| 3.74 | 2-Cyclopenten-1-one, 2,3-dimethyl- |
| 2.96 | 5-Hexen-2-one, 5-methyl-3-methylene- |
| 3.88 | Cyclohexene,3-propyl- |
| 7.11 | 3-Octyne |
| 1.23 | Hexanoic acid, 2-ethyl- |
| 0.49 | Hydrazine, 1-(2-ethyl-6-methylphenyl)- |
| 0.46 | n-Hexadecanoic acid |
| 1.12 | 11-Dodecen-1-ol, 2,4,6-trimethyl-, (R,R,R)- |
| 5.83 | Phenol |
| 2.93 | Phenol, 2-methyl- |
| 0.98 | Phenol, 2-ethyl- |
| 1.34 | Phenol, 2,4-dimethyl- |
| 0.86 | Phenol, 3,5-dimethyl- |
| 4.74 | Phenol, 4-ethyl- |
| 1.18 | Phenol, 3,4-dimethyl- |
| 0.51 | Phenol, 3-(1-methylethyl)-, methylcarbamate |
| 1.16 | Phenol, 2-ethyl-4-methyl- |
| 0.71 | Phenol, 3-ethyl-5-methyl- |
| 0.64 | Phenol, 4-ethyl-2-methoxy- |
| 0.47 | Phenol, 2-methyl-6-(2-propenyl)- |

TABLE 6a

List of all major chemical group compounds
Rice Straw + 80 g Water Without Catalyst

| Compounds | Area % |
|---|---|
| Aromatic | 4.15 |
| Alcohol | 2.41 |
| Alkane | 0 |
| Alkene | 2.07 |
| Cycloalkane | 42.61 |
| Ketonic | 13.12 |
| Phenolic | 21.35 |
| Fatty acid | 0 |
| Others | 14.29 |

Figure 3:
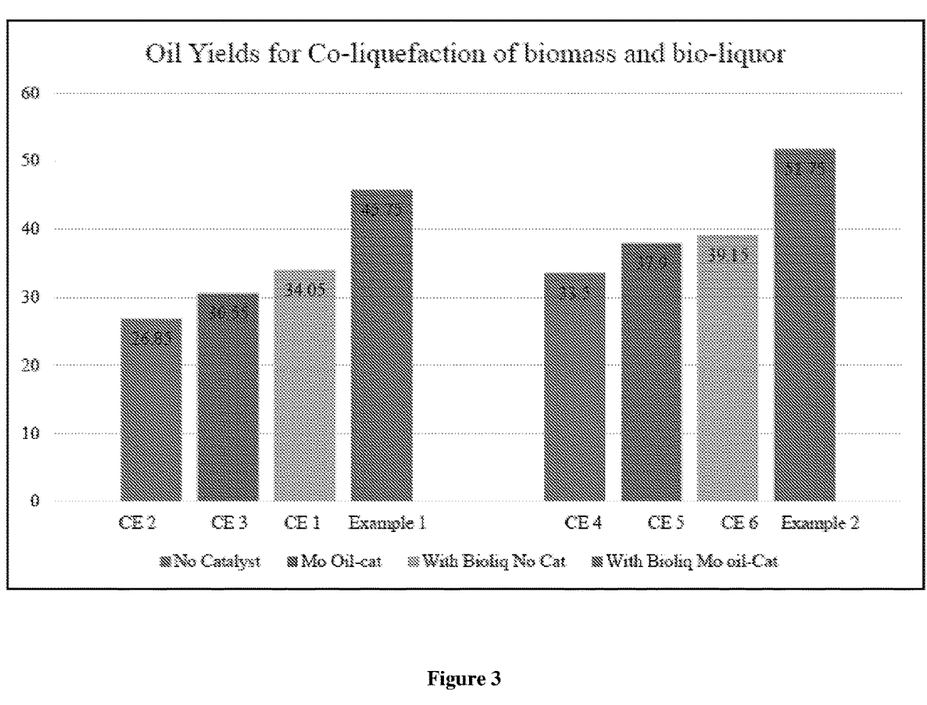
FIG. 3 shows the comparative oil yield for the examples 1-2 of the present invention and comparative examples.

Results: GC-MS analysis was conducted for each sample and found that the aromatics are formed. The yield of the oil stream obtained from the method of the present invention is provided in the table 6 below and FIG. 3. The results in the table and FIG. 3 demonstrated that the process of present invention provides high yield of the oil stream when compared to the comparative examples.

The yields of the solid residue and oil formed were calculated from the below reactions:

$$X_{SR}\% = (\text{Weight of Solid Residue} \times 100)/\text{Weight of feedstock} \quad (1)$$

$$X_{OIL}\% = (\text{Weight of Oil} \times 100)/\text{Weight of feedstock} \quad (2)$$

TABLE 6

Comparision of oil yield and chemical group compounds for rice husk

| | Example 1 | CE-1 | CE-2 | CE-3 |
|---|---|---|---|---|
| Conditions | T-593 K, P-23-25 Mpa | T-593 K, P-23-25 Mpa | T-593 K, P-23-25 Mpa | T-593 K, P-23-25 Mpa |
| Catalyst Type | Molybdenum oil soluble catalyst | Without Catalyst | Without Catalyst | Molybdenum oil soluble catalyst |
| Feedstock | Rice Husk (RH) | Rice Husk (RH) | Rice Husk (RH) | Rice Husk (RH) |
| Solvent | Bioliquor | Bioliquor | Water | Water |
| Catalyst Wt | 0.2 g | — | — | 0.2 g |
| Oil Yield | 45.75% | 34.05% | 26.85% | 30.55% |
| AROMATIC | 13.29 | 42.66 | 4.86 | 28.70 |
| ALCOHOL | 14.11 | 5.54 | 6.20 | 1.76 |
| ALKANE | 0 | 0 | 0 | 0 |
| ALKENE | 10.48 | 13.84 | 2.44 | 6.36 |
| CYCLOALKANE | 13.02 | 0 | 54.11 | 3.18 |
| KETONIC | 15.77 | 17.61 | 5.49 | 4.86 |
| PHENOLIC | 27.94 | 18.12 | 12.47 | 26.18 |
| OTHERS | 5.42 | 2.24 | 7.99 | 24.27 |

T-Temperature; P-Pressure

TABLE 7

Comparision of oil yield and chemical group compounds for rice straw

| | Example 2 | CE-4 | CE-5 | CE-6 |
|---|---|---|---|---|
| Conditions | T-593 K, P-23-25 Mpa | T-593 K, P-23-25 Mpa | T-593 K, P-23-25 Mpa | T-593 K, P-23-25 Mpa |
| Catalyst Type | Molybdenum oil soluble catalyst | Without Catalyst | Molybdenum oil soluble catalyst | Without Catalyst |
| Feedstock | Rice Straw (RS) | Rice Straw (RS) | Rice Straw (RS) | Rice Straw (RS) |
| Solvent | Bioliquor | Bioliquor | Water | Water |
| Catalyst Wt | 0.2 g | — | 0.2 | — |
| Oil Yield | 51.75% | 39.15% | 37.9% | 33.5% |
| AROMATIC | 46.04 | 10.34 | 8.11 | 4.15 |
| ALCOHOL | 1.37 | 1.52 | 0 | 2.41 |
| ALKANE | 10.8 | 0 | 0 | 0 |
| ALKENE | 1.26 | 2.64 | 2.19 | 2.07 |
| CYCLOALKANE | 2.70 | 0 | 5.31 | 42.61 |
| KETONIC | 8.72 | 8.93 | 21.27 | 13.12 |
| PHENOLIC | 29.10 | 15.47 | 58.52 | 21.35 |
| FATTY ACID | 0 | 24.31 | 0 | 0 |
| OTHERS | 0 | 4.50 | 4.61 | 14.29 |

T-Temperature; P-Pressure

A skilled artisan will appreciate that the quantity and type of each ingredient can be used in different combinations or singly. All such variations and combinations would be falling within the scope of present disclosure.

The foregoing examples are merely illustrative and are not to be taken as limitations upon the scope of the invention. Various changes and modifications to the disclosed embodiments will be apparent to those skilled in the art. Such changes and modifications may be made without departing from the scope of the invention.

ADVANTAGES OF THE PRESENT INVENTION

The present invention provides a method of converting of biomass feedstock to fuels and chemicals which gives high yield of oil stream.

The present invention provides a method of converting of biomass feedstock to fuels and chemicals that is useful in obtaining $C_8$-$C_{13}$ aromatics.

The present invention provides the feasibility to use bio-liquor, a waste stream from the 2G-ethanol plant, to produce good oil yield, thereby totally eliminating the dependence on pure water as solvent.

The present invention allows for the usage of very low amount of catalyst loading per biomass taken, to give high yield of oil stream majorily comprising hydrocarbons and phenolics.

We claim:

1. A method of producing fuels and chemicals from biomass feedstock comprising the steps of:
   (a) mixing biomass feedstock in a feedstock vessel and introducing the biomass feedstock into a hydrothermal liquefaction reactor;
   (b) processing a lignocellulose biomass in a biomass treatment unit to obtain a processed lignocellulose biomass and bioliquor and fermenting the processed lignocellulose biomass in a fermenter to obtain ethanol;
   (c) introducing the bioliquor stream into the hydrothermal liquefaction reactor comprising the biomass feedstock to obtain a mixture;
   (d) subjecting the mixture to hydrothermal liquefaction by adding a transition-metal catalyst to obtain a liquefied product;
   (e) collecting the liquefied product in a collection vessel and separating the liquefied product into a gaseous product and a gas-free product stream; and
   (f) separating the gas-free product stream into oil stream comprising fuels and chemicals, a solid phase, and an aqueous phase.

2. The method as claimed in claim 1, wherein the biomass feedstock is selected from rice straw, rice husk, saw dust, corn stover or any combinations thereof.

3. The method as claimed in claim 1, wherein the processing of lignocellulose biomass comprises the step of treating lignocellulose biomass with acid or base and $C_5$-$C_6$ sugars.

4. The method as claimed in claim 3, wherein the acid is selected from organic acid or inorganic acids and the base is sodium hydroxide or potassium hydroxide and $C_5$-$C_6$ sugar is xylose, arabinose, glucose, fructose or lignin.

5. The method as claimed in claim 1, wherein the bioliquor stream comprises sodium hydroxide and lignin.

6. The method as claimed in claim 1, wherein the hydrothermal liquefaction in step (d) is carried out at a temperature in the range of 120 deg C. to 400 deg C. and at a pressure in the range of 2 to 30 MPa.

7. The method as claimed in claim 1, wherein the hydrothermal liquefaction in step (d) is carried out at a temperature in the range of 180 deg C. to 350 deg C. and at a pressure in the range of 10 to 20 MPa.

8. The method as claimed in claim 1, wherein the hydrothermal liquefaction in step (d) is carried out in a time ranging from 5 minutes to 120 minutes.

9. The method as claimed in claim 1, wherein the gaseous product obtained in step (e) is routed for heat integration with feedstock heating.

10. The method as claimed in claim 1, wherein the separating of gas-free product stream further comprises separating of bleed stream and make-up liquid which is connected with the bio-liquor for further processing.

11. The method as claimed in claim 1, wherein the solid phase is subjected to purification comprising the steps of:
    purifying the solid phase to obtain purified solid product; and
    sending the purified solid product to solid char upgradation unit to obtain a final product.

12. A method of upgradation of oil stream obtained from the method of claim 1, wherein the method of upgradation is selected from:
    (a) mixing the oil stream with petroleum fractions in co-processing unit to obtain the hydrocarbons;
    (b) hydrotreating the oil stream in a hydrotreating unit to obtain diesel or jet range fuels;
    (c) cracking the oil stream using a fluid catalytic cracking unit in the presence of a catalyst to obtain light olefins and gasoline additive compounds; and
    (d) cracking the oil stream using a steam cracking unit to ethylene and propylene.

13. The method as claimed in claim 12, wherein the catalyst in the fluid catalytic cracking unit is selected from ZSM-5, beta-zeolite, y-zeolite or a combination thereof.

14. The method as claimed in claim 1, wherein the transition metal catalyst is a Fe, Mo, Ni, or Co based catalyst or iron powder, Ni powder, or a high Fe containing red mud powder catalyst.

15. The method as claimed in claim 1, wherein the transition metal catalyst is present in a concentration range of 0.1-10 wt % of solids loading.

16. The method as claimed in claim 1, wherein the biomass solids loading is present in a concentration range of 10-30 wt %.

17. The method as claimed in claim 1, wherein the fuels and chemicals are selected from alcohol, alkenes, aromatic, cycloalkane, ketonic, and phenolic compounds.

18. The method as claimed in claim 1, further comprising purifying the oil stream to obtain a purified oil stream.

19. The method as claimed in claim 18, further comprising upgrading the purified oil stream to obtain fuels and chemicals.

* * * * *